United States Patent
Golightly et al.

(10) Patent No.: US 8,859,810 B2
(45) Date of Patent: Oct. 14, 2014

(54) PROCESS FOR RECOVERING PERMANGANATE REDUCING COMPOUNDS FROM AN ACETIC ACID PRODUCTION PROCESS

(75) Inventors: Robert Glenn Golightly, Friendswood, TX (US); Oyeyemi Oyerinde, Houston, TX (US); Mark O. Scates, Houston, TX (US); Ronald D. Shaver, Houston, TX (US)

(73) Assignee: Celanese International Corporation, Irving, TX (US)

( * ) Notice: Subject to any disclaimer, the term of this patent is extended or adjusted under 35 U.S.C. 154(b) by 101 days.

(21) Appl. No.: 13/590,389

(22) Filed: Aug. 21, 2012

(65) Prior Publication Data

US 2014/0058131 A1  Feb. 27, 2014

(51) Int. Cl.
*C07C 51/42* (2006.01)

(52) U.S. Cl.
USPC .......................................... 562/608

(58) Field of Classification Search
CPC ................................ C07C 51/44; C07C 53/08
See application file for complete search history.

(56) References Cited

U.S. PATENT DOCUMENTS

| | | |
|---|---|---|
| 3,769,329 A | 10/1973 | Paulik et al. |
| 4,908,477 A | 3/1990 | Hartmann et al. |
| 5,001,259 A | 3/1991 | Smith et al. |
| 5,026,908 A | 6/1991 | Smith et al. |
| 5,144,068 A | 9/1992 | Smith et al. |
| 6,143,930 A | 11/2000 | Singh et al. |
| 6,339,171 B1 | 1/2002 | Singh et al. |
| 7,223,886 B2 | 5/2007 | Scates et al. |
| 7,855,306 B2 | 12/2010 | Zinobile et al. |
| 2005/0197509 A1* | 9/2005 | Picard et al. .................. 562/608 |
| 2006/0247466 A1* | 11/2006 | Zinobile et al. ............... 562/517 |
| 2009/0270651 A1 | 10/2009 | Zinobile et al. |
| 2011/0288333 A1* | 11/2011 | Shaver et al. ................. 562/608 |
| 2012/0090980 A1 | 4/2012 | Torrence et al. |
| 2012/0090981 A1* | 4/2012 | Torrence et al. ................ 203/45 |

OTHER PUBLICATIONS

Jones, J. H. (2000), "The Cativa™ Process for the Manufacture of Acetic Acid", Platinum Metals Review, 44 (3): 94-105.
International Search Report and Written Opinion for PCT/US2013/054915 mailed Oct. 16, 2013.

* cited by examiner

*Primary Examiner* — Karl J Puttlitz (57) ABSTRACT

This invention relates to processes for producing acetic acid and, in particular, to improved processes for recovering permanganate reducing compounds formed during the carbonylation of methanol in the presence of a carbonylation catalyst to produce acetic acid. Alkyl halides are removed or reduced from the recovered permanganate reducing compounds.

21 Claims, 2 Drawing Sheets

FIG. 1

FIG. 2 large US 8,859,810 B2

PROCESS FOR RECOVERING PERMANGANATE REDUCING COMPOUNDS FROM AN ACETIC ACID PRODUCTION PROCESS

FIELD OF THE INVENTION

This invention relates to processes for producing acetic acid. Specifically, the invention relates to improved processes for recovering permanganate reducing compounds (PRC's) formed during the carbonylation of methanol in the presence of a carbonylation catalyst to produce acetic acid. More specifically, it is to improved process for removing alkyl halides, such as methyl iodide, from the recovered PRC's.

BACKGROUND OF THE INVENTION

A widely used and successful commercial process for synthesizing acetic acid involves the catalyzed carbonylation of methanol with carbon monoxide. The catalysis contains rhodium and/or iridium and a halogen promoter, typically methyl iodide. The reaction is conducted by continuously bubbling carbon monoxide through a liquid reaction medium in which the catalyst is dissolved. The reaction medium also comprises methyl acetate, water, methyl iodide and the catalyst. Conventional commercial processes for carbonylation of methanol include those described in U.S. Pat. Nos. 3,769,329; 5,001,259; 5,026,908; and 5,144,068, the entire contents and disclosures of which are hereby incorporated by reference. Another conventional methanol carbonylation process includes the Cativa™ process, which is discussed in Jones, J. H. (2002), "The Cativa™ Process for the Manufacture of Acetic Acid," *Platinum Metals Review*, 44 (3): 94-105, the entire content and disclosure of which is hereby incorporated by reference.

The crude acetic acid product from the reactor is processed in a purification section to remove impurities and recover acetic acid. These impurities, which may be present in trace amounts, affect the quality of acetic acid, especially as the impurities are circulated through the reaction process, which, among other things, can result in the buildup of these impurities over time. Conventional purification techniques to remove these impurities include treating the acetic acid product streams with oxidizers, ozone, water, methanol, activated-carbon, amines, and the like. The treatments may also be combined with the distillation of the crude acetic acid product. However, the additional treatment of the final product adds cost to the process, and distillation of the treated acetic acid product can result in additional impurities being formed.

Processes for removing these impurities may also remove compounds in the reaction medium, such as the halogen promoter. Several processes have been taught for recovering the halogen promoter including treatment of vented streams and extraction.

Treatment of vented streams allows recovery of halogen promoters. For example, U.S. Pub. No. 2009/0270651 discloses a methanol carbonylation system that includes an absorber tower adapted for receiving a vent gas stream and removing methyl iodide therefrom with a scrubber solvent, the absorber tower being coupled to first and second scrubber solvent sources which are capable of supplying different first and second scrubber solvents. A switching system including valves alternatively provides first or second scrubber solvents to the absorber tower and returns the used solvent and absorbed material to the carbonylation system to accommodate different operating modes.

Extraction may also recover halogen promoters from the carbonylation products. For example, U.S. Pat. No. 4,908,477 discloses separating organic iodine compounds from carbonylation products of methanol, methyl acetate and dimethyl ether and from mixtures of such carbonylation products by a process wherein the iodine compounds are removed by liquid phase extraction with a non-aromatic hydrocarbon.

The methods for recovering halogen promoters are not able to remove other impurities. In particular, the impurities that decrease the permanganate time of the acetic acid are not removed when recovering halogen promoters. Permanganate time is a quality test commonly used in the acetic acid industry to determine the amount of impurities present in an acetic acid product. These impurities include saturated and unsaturated carbonyl compounds, generally referred to as permanganate reducing compounds (PRC's). PRC's, may include, for example, compounds such as acetaldehyde, acetone, methyl ethyl ketone, butyraldehyde, crotonaldehyde, 2-ethyl crotonaldehyde, 2-ethyl butyraldehyde and the like, and the aldol condensation products thereof. These compounds are removed through one or more columns and extraction units.

The art has disclosed that PRC's present in the crude acetic acid product streams generally concentrate in the overhead stream from the light ends column. Accordingly, the light ends column overhead stream has been treated with an amine compound (such as hydroxylamine), which reacts with the carbonyl compounds to form derivatives that can be separated from the remaining overhead stream by distillation, resulting in an acetic acid product with improved permanganate time.

It has been disclosed in U.S. Pat. Nos. 6,143,930 and 6,339,171, the entireties of which are incorporated herein by reference, that it is possible to significantly reduce undesirable impurities in the acetic acid product by performing a multi-stage purification on the light ends column overhead stream. These patents disclose a purification process in which the light ends overhead stream is distilled twice, in each case taking the acetaldehyde overhead and returning a methyl iodide-rich residue to the reactor. The acetaldehyde-rich distillate obtained after the two distillation steps is optionally extracted with water to remove the majority of the acetaldehyde for disposal, leaving a significantly lower acetaldehyde concentration in the raffinate that is recycled to the reactor.

In addition, it has been disclosed in U.S. Pub. No. 2006/0247466, the entirety of which is incorporated herein by reference, that it is possible to reduce undesirable impurities in the acetic acid product by subjecting the light ends overhead stream to a single distillation to obtain an overhead stream. The overhead stream is then subjected to an extraction that selectively removes and/or reduces PRC's.

U.S. Pat. No. 7,223,886, the entirety of which is incorporated herein by reference, discloses a method for reducing the formation of alkyl iodides and $C_3$ to $C_8$ carboxylic acids by removing PRC's from the light phase of the condensed light ends overhead stream, including (a) distilling the light phase to yield a PRC enriched overhead stream; and (b) extracting the overhead stream with water in at least two consecutive stages and separating therefrom one or more aqueous streams containing PRC's.

U.S. Pat. No. 7,855,306, the entirety of which is incorporated herein by reference, discloses a process for reduction and/or removal of PRC's from a carbonylation product by (a) separating the carbonylation product to provide a vapor overhead stream; (b) distilling the vapor overhead stream to yield a low boiling overhead vapor stream; (c) condensing and separating the low boiling overhead vapor stream to form a condensed light liquid phase; (d) distilling the condensed light liquid phase in a single distillation column to form a second vapor phase stream enriched with PRC's; and (e) condensing and extracting the second vapor phase stream with water to obtain an aqueous acetaldehyde stream comprising PRC's.

U.S. Pub. No. 2012/0090981, the entirety of which is incorporated herein by reference, discloses a process for removing PRC's from a crude acetic acid composition by (a) extracting the light phase to obtain an aqueous stream comprising at least one PRC and (b) separating the aqueous stream in a distillation column to yield an overhead stream enriched with PRC's.

The effluent of the extraction units comprises the PRC's that are removed from the acetic acid production process. The effluent may also comprise impurities that may result in a loss of the compounds in the reactor and result in effluent streams that are more expensive and difficult to treat.

While the above-described processes have been successful in reducing and/or removing PRC's from the carbonylation system, further improvements can still be made for recovering PRC's.

SUMMARY OF THE INVENTION

In one embodiment, the present invention is directed to a process for recovering permanganate reducing compounds (PRC's) from a crude acetic acid composition, the process comprising the step of separating the crude acetic acid composition in a light ends column into an overhead stream and an acetic acid product stream. Preferably, the overhead stream comprises methyl iodide, water, methyl acetate, and at least one PRC, and an acetic acid product stream. PRC's, may include acetaldehyde, acetone, methyl ethyl ketone, butyraldehyde, crotonaldehyde, 2-ethyl crotonaldehyde, 2-ethyl butyraldehyde, the aldol condensation products thereof, or mixtures thereof. The process further comprises the step of separating a portion of the overhead stream using a first distillation columns to obtain a stream enriched in the at least one PRC, wherein the enriched stream further comprises at least some of the methyl iodide from the overhead stream. The process further comprises separating a portion of the enriched stream in a second distillation column to obtain a distillate comprising methyl iodide and a residue comprising the at least one PRC. Preferably, the ratio of methyl iodide to PRC's in the residue is less than the ratio of methyl iodide to PRC's in the enriched stream.

The residue may comprise less than 1 wt. % methyl iodide, e.g., less than 0.01 wt. %. At least 80%, and more preferably at least 95%, of the methyl iodide in the portion of the PRC's stream is separated into the distillate. At least 80%, and more preferably at least 95%, of the at least one PRC in the portion of the PRC's stream is separated into the residue.

In one embodiment, the process further comprises the step of using an extractive agent in the second distillation column, e.g., an extractive distillation column, to extract at least one PRC into the residue. Preferably, the extractive agent is selected from the group consisting of water, glycols, glycerol, high boiling alcohols, or mixtures thereof. In one embodiment, a mass flow ratio of the portion of the PRC's stream and the extractive agent is at least 1:1. The extractive agent may be water that is fed in the top half of the extractive distillation column. In one embodiment, the process further comprises the step of recovering the extractive agent from the residue to yield a PRC's product that is reduced in water content. Once the extractive agent is removed from the residue, the process of the invention obtains a PRC's product having a reduced water content of less than 10 wt. % water.

The process further comprises the step of extracting the enriched stream in a liquid-liquid extractor with an extractive solvent to obtain a PRC's stream and a raffinate comprising methyl iodide. The extractive solvent may comprise water. In one embodiment, the PRC's stream comprises the at least one PRC and from 0.01 to 5 wt. % methyl iodide.

In another embodiment, the present of the invention comprises recovering permanganate reducing compounds (PRC's) from a crude acetic acid composition, the process comprising the steps of: separating the crude acetic acid composition in a light ends column into an overhead stream comprising methyl iodide, water, methyl acetate, and at least one PRC, and an acetic acid product stream; separating a portion of the overhead stream, either an organic or aqueous portion thereof, using one or more distillation columns to obtain a stream enriched in the at least one PRC, wherein the enriched stream further comprises at least some of the methyl iodide from the overhead stream; extracting the enriched stream in a liquid-liquid extractor with an extractive solvent to obtain a PRC's stream and a raffinate comprising methyl iodide, wherein the PRC's stream comprises the at least one PRC and from 0.01 to 5 wt. % methyl iodide; and separating a portion of the PRC's stream in an extractive distillation column using an extractive agent to obtain a distillate comprising methyl iodide and a residue comprising the at least one PRC and extractive agent, wherein the ratio of methyl iodide to PRC's in the residue is less than the ratio of methyl iodide to PRC's in the PRC's stream.

BRIEF DESCRIPTION OF DRAWINGS

The present invention will be better understood in view of the appended non-limiting figures, wherein.

DETAILED DESCRIPTION OF THE INVENTION

The present invention generally relates to recovery of PRC's, such as acetaldehyde, and reducing the amount of alkyl halides, such as halogen promoters, therein from the PRC residue stream. In preferred embodiments, the alkyl halide is methyl iodide (MeI). Due to the reaction conditions and reaction medium, PRC's may be formed as side products that cause impurities when making acetic acid. When removing PRC's from the crude acetic acid product, the halogen promoters may pass through into purge streams and as such, the resulting PRC's stream comprises the halogen promoters. Although the amount of halogen promoters in the purge streams may be relatively small, the cost associated with purging the halogen promoters may be significant. Embodiments of the present invention advantageously increase the amounts of halogen promoters that may be removed from the PRC's stream to yield a purified PRC's stream, thereby reducing costs, improving efficiency and reducing the need to treat purge streams. The purified PRC's stream with reduced level of halogen promoters may be used as raw materials for other processes. Moreover, the halogen promoters recovered therefrom may be recycled to the carbonylation process.

In one embodiment of the present invention, PRC's are preferably recovered with a PRC recovery system (PRS) that comprises one or more distillation column. PRC's, may include acetaldehyde, acetone, methyl ethyl ketone, butyraldehyde, crotonaldehyde, 2-ethyl crotonaldehyde, 2-ethyl butyraldehyde, the aldol condensation products thereof, or mixtures thereof. Exemplary PRS include those described in U.S. Pat. Nos. 7,855,306, 7,223,886; 7,855,306; 6,143,930 and 6,339,171, and U.S. Pub. No. 2012/0090981, the entire contents and disclosures of which is hereby incorporated by reference. A stream enriched with PRC's may be separated from the acetic acid production process and introduced to the PRS. This stream may also comprise alkyl halides.

In one embodiment, the alkyl halides may be recovered from one or more treated streams of the PRS. Generally these treated streams are purged from the system. Advantageously this embodiment removes the alkyl halides from the purge streams and may reduce costs for treating the purge streams.

Although it is preferred to recover methyl iodide for returning to the reactor, other alkyl halides such as ethyl iodide, propyl iodide, butyl iodide, pentyl iodide, hexyl iodide, and isomers thereof, may also be removed from the treated streams of the PRS. The alkyl halides, including halogen promoters, may cause corrosion in the system by forming hydroiodic (HI) acid in distillation portions of the PRS as described in several reactions that involve the halogen promoter, methyl iodide. As an example:

MeI+MeOH→Me$_2$O+HI          (I)

MeI+H$_2$O→MeOH+HI          (II)

MeI+MeCOOH→MeCOOMe+HI          (III)

In one embodiment, one or more distillation column is used to recover PRC's. Preferably, two distillation columns are used to recover PRC's. In one embodiment, a substantial amount of methyl acetate is removed in the residue of the first distillation column and returned to the reaction zone. In addition, the distillate is enriched with PRC's and is deficient with methyl acetate, methanol, and/or acetic acid. The distillate stream is sent to a second distillation column to further remove any remaining methyl iodide to yield a PRC stream in the residue.

In another embodiment, alkyl halides may be removed using an extractive solvent in a liquid-liquid extractor and the extractant, which would be enriched in PRC's, is further purified using an extractive agent in an extractive distillation column. The combination of the extractor and extractive distillation column greatly improves the recovery of the alkyl halides and purification of the PRC's stream. The liquid-liquid extractive solvent comprises water, dimethyl ether, and mixtures thereof. In one embodiment, a suitable extractive agent may be selected from the group consisting of water, glycols, glycerol, high boiling alcohols, and mixtures thereof. Preferably, the extractive solvent and extractive agent may be water.

In another embodiment, an extractive agent may be used with the second distillation column. The use of the extractive agent, such as water, may remove methyl iodide from the PRC enriched stream thereby yielding a further enriched PRC stream. The extractive agent may be recovered in an extractive agent recovery column and returned to the second distillation column for use.

This invention relates to processes for the production of acetic acid and, in particular, to improved processes for the recovery of permanganate reducing compounds (PRC's) formed during the carbonylation of methanol in the presence of a Group VIII metal carbonylation catalyst. PRC's, may include, for example, compounds such as acetaldehyde, acetone, methyl ethyl ketone, butyraldehyde, crotonaldehyde, 2-ethyl crotonaldehyde, and 2-ethyl butyraldehyde and the like, and the aldol condensation products thereof. More specifically, this invention relates to improved processes for removing and recovering PRC's or their precursors from an acetic acid separation system that is used to purify a crude acetic acid product. More specifically, this invention relates to improved process for removing and recovering methyl iodide.

The present invention may be appreciated in connection with, for example, the carbonylation of methanol with carbon monoxide in a homogeneous catalytic reaction system comprising a reaction solvent, methanol and/or reactive derivatives thereof, a Group VIII catalyst, at least a finite concentration of water, and optionally an iodide salt.

Suitable Group VIII catalysts include rhodium and/or iridium catalysts. When a rhodium catalyst is utilized, the rhodium catalyst may be added in any suitable form such that rhodium is in the catalyst solution as an equilibrium mixture including [Rh(CO)$_2$I$_2$]$^-$ anion as is well known in the art. Iodide salts optionally maintained in the reaction mixtures of the processes described herein may be in the form of a soluble salt of an alkali metal or alkaline earth metal or a quaternary ammonium or phosphonium salt or mixtures thereof. In certain embodiments, the catalyst co-promoter is lithium iodide, lithium acetate, or mixtures thereof. The salt co-promoter may be added as a non-iodide salt that will generate an iodide salt. The iodide catalyst stabilizer may be introduced directly into the reaction system. Alternatively, the iodide salt may be generated in-situ since under the operating conditions of the reaction system, a wide range of non-iodide salt precursors will react with methyl iodide or hydroiodic acid in the reaction medium to generate the corresponding co-promoter iodide salt stabilizer. In some embodiments, the rhodium catalyst concentration in the liquid reaction medium may be in the range of 100 wppm to 6000 wppm. For additional detail regarding rhodium catalysis and iodide salt generation, see U.S. Pat. Nos. 5,001,259; 5,026,908; 5,144,068 and 7,005,541, the entireties of which are hereby incorporated by reference.

When an iridium catalyst is utilized, the iridium catalyst may comprise any iridium-containing compound which is soluble in the liquid reaction composition. The iridium catalyst may be added to the liquid reaction composition for the carbonylation reaction in any suitable form which dissolves in the liquid reaction composition or is convertible to a soluble form. Examples of suitable iridium-containing compounds which may be added to the liquid reaction composition include: IrCl$_3$, IrI$_3$, IrBr$_3$, [Ir(CO)$_2$I]$_2$, [Ir(CO)$_2$Cl]$_2$, [Ir(CO)$_2$Br]$_2$, [Ir(CO)$_2$I$_2$]$^-$H$^+$, [Ir(CO)$_2$Br$_2$]$^-$H$^+$, [Ir(CO)$_2$I$_4$]$^-$H$^+$, [Ir(CH$_3$)I$_3$(CO$_2$)]$^-$H$^+$, Ir$_4$(CO)$_{12}$, IrCl$_3$.3H$_2$O, IrBr$_3$.3H$_2$O, Ir$_4$(CO)$_{12}$, iridium metal, Ir$_2$O$_3$, Ir(acac)(CO)$_2$, Ir(acac)$_3$, iridium acetate, [Ir$_3$O(OAc)$_6$(H$_2$O)$_3$][OAc], and hexachloroiridic acid [H$_2$IrCl$_6$]. Chloride-free complexes of iridium such as acetates, oxalates and acetoacetates are usually employed as starting materials. The iridium catalyst concentration in the liquid reaction composition may be in the range of 100 to 6000 wppm. The carbonylation of methanol utilizing iridium catalyst is well known and is generally described in U.S. Pat. Nos. 5,942,460; 5,932,764; 5,883,295; 5,877,348; 5,877,347 and 5,696,284, the entireties of which are hereby incorporated by reference.

Halogen promoters are generally used in combination with the Group VIII metal catalyst component. Methyl iodide is a preferred as the halogen promoter. Preferably, the concentration of halogen promoter in the liquid reaction composition is in the range 1 to 50% by weight, preferably 2 to 30% by weight.

The halogen promoter may be combined with a salt stabilizer/co-promoter compound, which may include salts of a metal of Group IA or Group IIA, a quaternary ammonium, phosphonium salt or mixtures thereof. Particularly preferred are iodide or acetate salts, e.g., lithium iodide or lithium acetate.

Other promoters and co-promoters may be used as part of the catalytic system of the present invention as described in U.S. Pat. No. 5,877,348, the entirety of which is hereby incorporated by reference. Suitable promoters are selected from ruthenium, osmium, tungsten, rhenium, zinc, cadmium, indium, gallium, mercury, nickel, platinum, vanadium, titanium, copper, aluminum, tin, antimony, and are more preferably selected from ruthenium and osmium. Specific co-promoters are described in U.S. Pat. No. 6,627,770, the entirety of which is incorporated herein by reference.

A promoter may be present in an effective amount up to the limit of its solubility in the liquid reaction composition and/or any liquid process streams recycled to the carbonylation reactor from the acetic acid recovery stage. When used, the promoter is suitably present in the liquid reaction composition at a molar ratio of promoter to metal catalyst of 0.5:1 to 15:1, preferably 2:1 to 10:1, more preferably 2:1 to 7.5:1. A suitable promoter concentration is 400 to 5000 wppm.

In one embodiment, the temperature of the carbonylation reaction is preferably from 150° C. to 250° C., e.g., from 155° C. to 235° C., or from 160° C. to 220° C. The pressure of the carbonylation reaction is preferably from 10 to 200 bar, preferably 10 to 100 bar, most preferably 15 to 50 bar. Acetic acid is typically manufactured in a liquid phase reaction at a temperature from 160° C. to 220° C. and a total pressure from 20 to 50 bar.

The separation system preferably controls water and acetic acid content in the reactor, as well as throughout the system and, optionally, controls the removal of PRC's. PRC's may include, for example, compounds such as acetaldehyde, acetone, methyl ethyl ketone, butyraldehyde, crotonaldehyde, 2-ethyl crotonaldehyde, 2-ethyl butyraldehyde and the like, and the aldol condensation products thereof.

Figure 1:
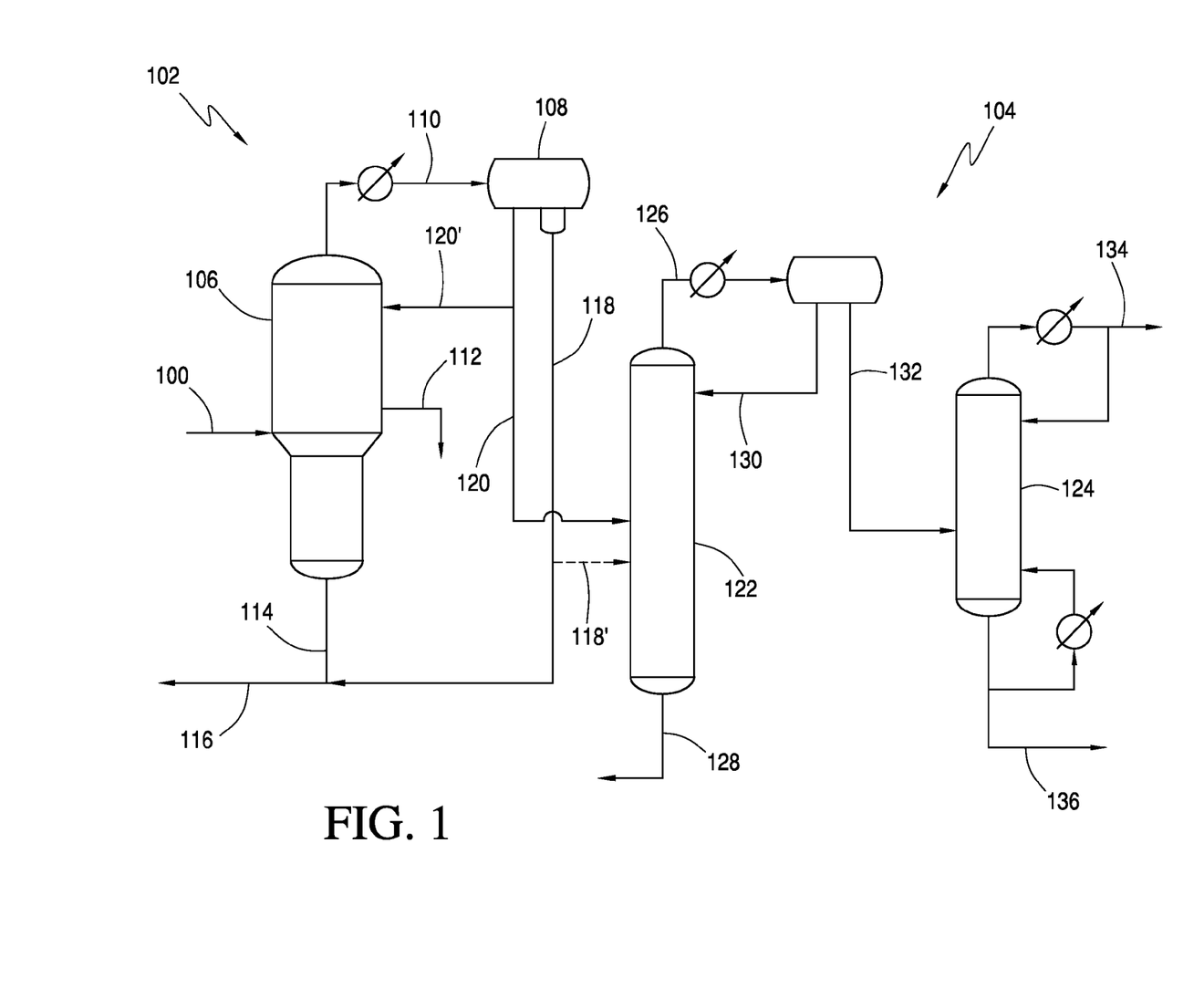
FIG. 1 illustrates an exemplary PRC recovery system (PRS) according to one embodiment of the invention.

Referring to FIG. 1, a crude acetic acid product 100 is obtained from a reaction section (not shown) and directed to a purification section 102. Reaction sections for the production of acetic acid are known in the art, and are disclosed in U.S. Pat. Nos. 5,942,460; 5,932,764; 5,883,295; 5,877,348; 5,877,347 and 5,696,284, the entire contents and disclosures of which are hereby incorporated by reference. Purification section 102 comprises light ends column 106, overhead decanter 108, and PRC recovery system (PRS) 104. In further embodiments, the purification section 102 may comprise drying columns, guard beds, vent scrubbers, and/or heavy ends columns. Guard beds are described in U.S. Pat. Nos. 4,615,806, 4,894,477, and 6,225,498, the entire contents and disclosures of which are hereby incorporated by reference.

In light ends column 106, crude acetic acid product 100 is separated into an overhead vapor stream 110, a purified acetic acid product that preferably is removed via a side stream 112, and an optional light ends residue stream 114. Acetic acid removed via side stream 112 preferably is subjected to further purification, such as in drying column (not shown) for selective separation of acetic acid from water and/or an optional heavy ends column (not shown), as described in U.S. Pat. No. 6,627,770, the entire contents and disclosures of which are hereby incorporated by reference, and optional guard beds (not shown). Optionally, a portion of side stream 112 may be recirculated to the light ends column (not shown), preferably to a point below where side stream 112 was removed from light ends column, in order to improve the separation.

The light ends residue stream 114 typically will comprise heavy components, acetic acid, water, and entrained catalyst, it may be beneficial to recycle all or a portion of the light ends residue stream 114 to the process via recycle stream 116.

One or more recycle feed streams 116, may be fed to the reactor section or anywhere else in the carbonylation process. Although one recycle feed stream 116 is shown in FIG. 1, there may be multiple streams that are fed separately to the reactor and/or process. As discussed below the recycle feed streams 116 may comprise the components of the reaction medium, as well as residual and/or entrained catalyst and acetic acid.

Overhead stream 110 may comprise an alkyl halide, methyl acetate, hydrogen, water, methanol, PRC's, acetic acid, or mixtures thereof. It has been disclosed in U.S. Pat. Nos. 6,143,930 and 6,339,171 that there is generally a higher concentration of PRC's, and in particular acetaldehyde, in overhead stream 110 exiting light ends column 106 than in residue stream 114 exiting light ends column 106.

Overhead stream 110 is preferably condensed and directed to an overhead phase separation unit, as shown by overhead decanter 108. Conditions are desirably maintained in the process such that overhead stream 110, once in decanter 108, will biphasically separate into a light phase (aqueous) and a heavy phase (organic). Generally, overhead stream 110 is cooled to a temperature sufficient to condense and separate the alkyl halide, methyl acetate, PRC's, other carbonyl components and water into two phases. Non-condensable gases may be removed by a vent stream (not shown). In one embodiment, overhead vapor stream from the light ends column 106 may bypass condenser and decanter 108 and be fed directly to distillation column 122.

The condensed heavy phase in decanter 108 will generally comprise an alkyl halide, methyl acetate, PRC's, or mixtures thereof. The condensed heavy liquid phase in decanter 108 can be conveniently recirculated, either directly or indirectly, to the process via stream 118 and returned to the reaction section via recycle line 116. As discussed below, in some optional embodiments, a portion or all of heavy liquid phase may be fed to PRS 104. This may be in combination with a portion or all of the light liquid phase in stream 120.

The condensed light phase in decanter 108 preferably comprises water, acetic acid, and PRC's, as well as quantities of the alkyl halide, e.g., methyl iodide, methyl acetate, methanol, and/or alkyl iodides. The light phase exits decanter 108 via stream 120. A portion, e.g., aliquot portion, of light phase stream is recycled to the top of the light ends column 106 as reflux stream 120'. A second portion, e.g., aliquot portion, of the light phase stream optionally may be recycled to the reactor as shown by recycle stream (not shown), when additional water is desired or needed in the reactor.

Figure 2:
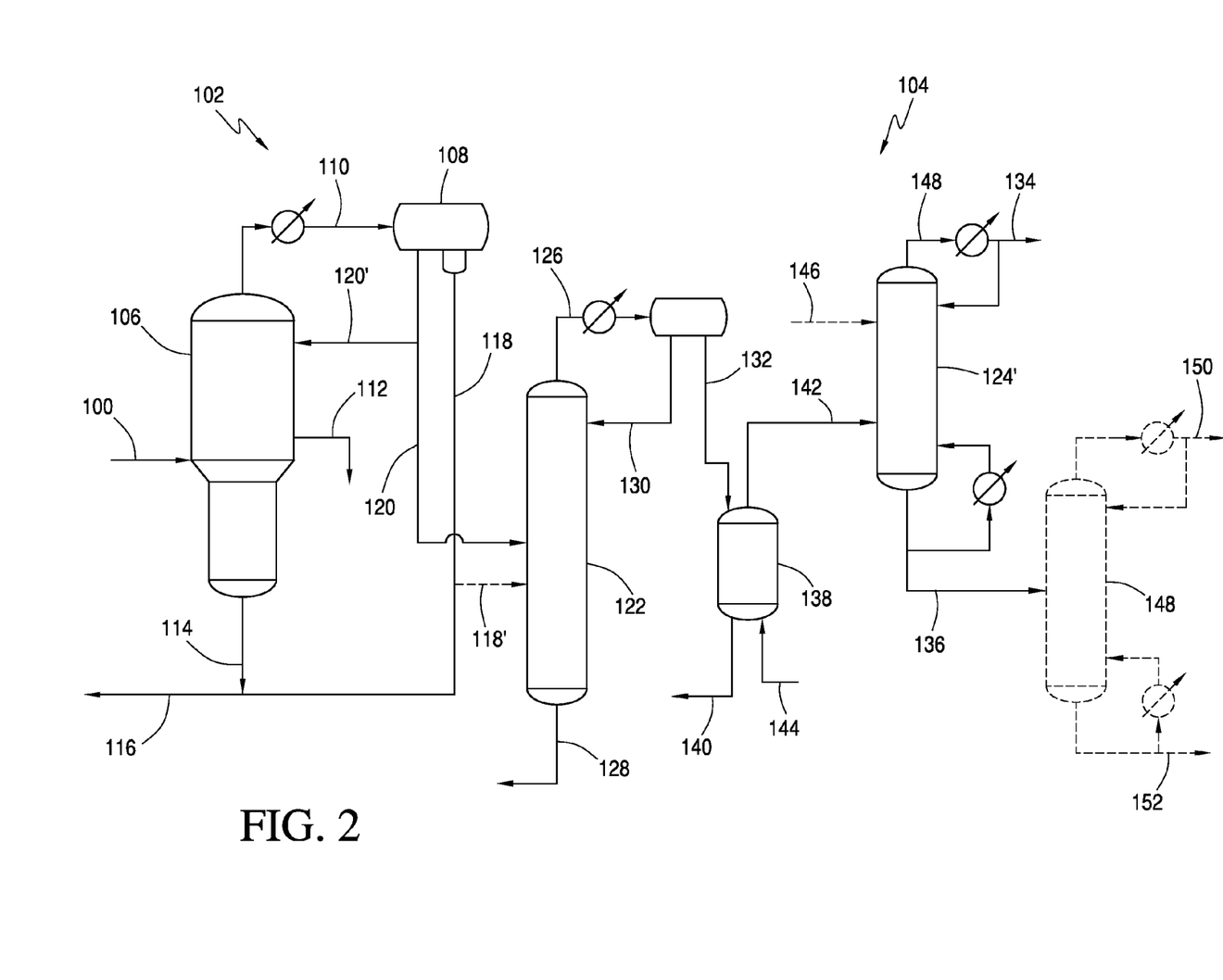
FIG. 2 illustrates an exemplary PRS having a combination of liquid-liquid extraction and an extractive distillation column according to one embodiment of the invention.

In one embodiment, a portion or all of light phase stream 120 is directly or indirectly introduced to PRS 104. Optionally, a portion or all of heavy phase stream 118' may be directly or indirectly introduced to PRS 104. In FIG. 1, PRS 104 comprises distillation columns 122 and 124. In FIG. 2, PRS 104 further comprises a liquid-liquid extractor 138, extractive distillation column 124', and recovery column 148. In further embodiments, the PRS may comprise two or more distillation columns and one or more extractors. An exemplary two-stage distillation PRS comprising one or more extractors is described in U.S. Pat. No. 7,223,886, and is incorporated by reference in its entirety herein. An exemplary single stage PRS, similar to those shown in FIG. 1, is described in U.S. Pat. No. 7,855,306, and is incorporated by reference in its entirety herein.

As shown in FIG. 1, light phase stream 120 is directed to distillation column 122 to produce an overhead PRC stream 126 and a bottoms stream 128. The overhead PRC stream 126 is enriched with PRC's, for example acetaldehyde and the residue stream 128 enriched in methyl iodide. Overhead PRC stream 126 is deficient with methyl acetate, methanol, and/or acetic acid, and more preferably deficient in all three, with respect to light phase 120. Bottoms stream 128 is enriched with methyl acetate, methanol, and/or acetic acid (desirably all three) with respect to the overhead PRC stream 126. Bottoms stream 128 can be, and preferably is, recycled back to light ends column 106 via decanter 108. In one embodiment, bottoms stream 128 comprises less than 500 wppm of alkyl halides, e.g., less than 200 wppm or less than 100 wppm.

A portion of overhead PRC stream 126 can be refluxed back to distillation column 122 via stream 130. In FIG. 1, a second portion of overhead PRC stream 132 may be introduced between the middle and bottom part of second distillation column 124. Although not shown, second distillation column 124 may be an extractive column. Overhead PRC stream 132 is separated to produce a distillate stream 134 and a residue stream 136. The distillate stream 134 is deficient with PRC's and enriched with methyl iodide and methyl acetate. Residue stream 136 is enriched with PRC's and preferably is substantially free of alkyl halides, e.g., less than 200 wppm, less than 100 wppm, or less than 50 wppm.

In one embodiment, the ratio of methyl iodide to PRC's in residue stream 136 is less than the ratio of methyl iodide to PRC's in PRC stream 132. As such, the amount of methyl iodide in residue 136 is less than the amount of methyl iodide in PRC stream 132. In another words, the majority of methyl iodide in PRC stream 132 is removed to the distillate in line 134.

Second distillation column 124 forms an overhead distillate, which is withdrawn in line 134, and which may be condensed and refluxed, for example, at a ratio from 30:1 to 1:30, e.g., from 25:1 to 1:25 or from 1:5 to 5:1. The overhead distillate stream 134 is enriched with methyl iodide, methyl acetate, dimethyl ether, methanol, water and/or acetic acid with respect to the residue in stream 136. The distillate in line 134 comprises the majority of halogen promoters and/or alkyl iodides in PRC stream 132, e.g., at least 85% of the halogen promoters and/or alkyl iodides in the PRC stream 132, e.g., at least 90% or at least 95%. In terms of ranges, distillate in line 134 may comprise 70 to 99.9% halogen promoters and/or alkyl iodides in the PRC stream, e.g., 80 to 99.8%, or 85 to 99.5%.

In distillation column 124, the majority of PRC's is recovered from PRC stream 132 and is withdrawn, preferably continuously, as a residue in line 136. For example, the residue stream comprises at least 85% of the PRC's in the PRC stream 132, e.g., at least 90% or at least 95%. In terms of ranges, residue stream 136 may comprise 70 to 99.9% PRC's in the PRC stream, e.g., 80 to 99.8%, or 85 to 99.5%. In a preferred embodiment, residue stream 136 contain substantially no alkyl halides (methyl iodide), e.g., contains less than 1 wt. %, less than 0.5 wt. %, or less than 0.1 wt. %.

Distillate stream 134 comprises the remaining halogen promoter and/or alkyl iodides in PRC stream 132 and is condensed and returned to the carbonylation process. Distillate stream 134 primarily comprises halogen promoter, and may also comprise one or more alkyl iodides selected from the group consisting of ethyl iodide, propyl iodide, butyl iodide, pentyl iodide, hexyl iodide, and isomers and mixtures thereof.

Depending on the amount of methyl iodide in PRC stream 132, a liquid-liquid extractor may be used in the PRS to remove methyl iodide. This may allow a combination of a liquid-liquid extraction and an extractive distillation process to remove alkyl halides from the recovered PRC's. As shown in FIG. 2, a second portion of overhead PRC stream 132 is fed to liquid-liquid extractor 138. Overhead PRC stream 132 is extracted with an extractive solvent feed stream 144 to produce raffinate 140, which comprises primarily an alkyl halide and aqueous stream 142, which comprises water, at least one PRC, an alkyl halide, or mixtures thereof. The relative portion of alkyl halides, including methyl iodide, is larger in raffinate 140 than aqueous stream 142. In addition to methyl iodide, aqueous stream 142 may also comprise one or more $C_{2+}$ alkyl halides. The amount of methyl iodide in aqueous stream 142 may be low and is preferably less than 6 wt. %, e.g., less than 3 wt. % or less than 0.5 wt. %. The extractive solvent is fed to liquid-liquid extractor 138 via extractive solvent feed stream 144. In some embodiments the extractive solvent is water. Raffinate 140 may be recycled back to the process via recycle stream 116. In some embodiments, raffinate 140 is directed to decanter 108 or stream 118. In some embodiments, raffinate 140 is directed to a downstream distillation system (not shown).

Accordingly, it is desirable that the liquid-liquid extraction be conducted at a combination of temperature and pressure such that the extractor contents can be maintained in the liquid state. Moreover, it is desirable to minimize the temperatures to which aqueous stream 142 is exposed to minimize the likelihood of polymerization and condensation reactions involving acetaldehyde. In some embodiments, extraction is conducted at a temperature from 10° C. to 40° C.

Although the specific compositions of aqueous stream 142 may vary widely, it is preferred that a majority of the alkyl halides in stream 132 pass through to raffinate 140. In one embodiment, at least 70% of the alkyl halides in stream 132 pass through to raffinate 140, e.g., more preferably at least 85% or at least 95%. In particular for methyl iodide, at least 70% of the methyl iodide in stream 132 passes through to raffinate 140, e.g., more preferably at least −85% or at least 95%. In addition, raffinate 140 preferably comprises a low weight percent of PRC's, e.g., less than 10 wt. %, or more preferably less than 5 wt. %. In one embodiment, aqueous stream 142 preferably comprises substantially all of the PRC's in stream 132, e.g., at least 90% of the PRC's from stream 132, or at least 99%.

Although aqueous stream 142 comprises substantially all of the PRC's in stream 132, a small amount of the alkyl halides remains therein. In one embodiment, aqueous stream 142 may comprise less than 5 wt. % methyl iodide, less than 3 wt. %, or less than 2 wt. %. In one embodiment, aqueous stream 144 may comprise less than 5 wt. % methyl acetate, e.g., less than 3 wt. % or less than 1 wt. %. Aqueous stream 144 may also comprise less than 10 wt. % dimethyl ether, less than 8 wt. % or less than 5 wt. %. Thus, it is beneficial to further recover the alkyl halides from the aqueous stream so that they may be recycled to carbonylation reaction zone. Furthermore, the removal of the remaining amount of alkyl halides would allow a purified PRC's stream to be use in other processes.

To remove alkyl halide, an extractive distillation column 124' may be used in place of distillation column 124. In an embodiment, aqueous stream 142 may be fed to distillation column 124 along with an extractive agent 146. Distillation column 124 separates aqueous stream 142 into a distillate in line 134 and a residue in line 136. Distillate in line 134 comprises a significant portion of the alkyl halides in aqueous stream 142, e.g., comprises a majority of the alkyl halides, more than 80%, more than 90% or more than 95%.

Residue in line 136 comprises the majority of the PRC's in aqueous stream 142 and extractive agent. Residue stream in line 136 contains PRC's and may be further separated in column 148 to recover a purified PRC's stream in line 150 and an extractive agent stream in line 152.

Aqueous stream 142 may be introduced between the middle and bottom part of extractive distillation column 124'. Extractive agent, as described above, is also introduced to extractive distillation column 124' via line 146 to aid with the separation of PRC's and alkyl halides. Depending on the type of extractive agent, extractive agent in line 146 may be introduced above the feed point of aqueous stream 142. Alternatively, the extractive agent may be mixed with aqueous stream 142 and co-fed to extractive distillation column 124'. Preferably, the extractive agent is fed at the top half of the extractive distillation column. In the case where water is used as the extractive agent the water content in the feed to the column may be sufficient to achieve the extractive distillation effect. Water feed to the liquid-liquid extraction unit may be varied to achieve the desired water content.

The amount of extractive agent fed to extractive distillation column 124' may vary widely depending on the concentration of PRC's in aqueous stream 142. In terms of mass flow ratios of PRC's stream and the extractive agent fed to the extractive distillation column 124' is at least 0.01:1, e.g., at least 1:1 or at least 4:1. Higher concentrations of extractive agent may be tolerated in some embodiments. In one embodiment, suitable extractive agent may be selected from the group consisting of water, glycols, glycerol, high boiling alcohols, and mixtures thereof.

When extractive distillation column 124' is operated at 294 kPa, the temperature of the distillate existing in line 124' preferably is from 0° C. to 60° C., e.g., from 5° C. to 40° C. or from 10° C. to 25° C. The residue in line 136 may comprise PRC's and the extractive agent. The temperature of the residue exiting in line 136 preferably is from 40° C. to 140° C., e.g., from 60° C. to 120° C. or from 80° C. to 100° C. In some embodiments, the pressure of extractive distillation column 128 may range from 90 kPa to 450 kPa, e.g., from 100 kPa to 400 kPa. Exemplary compositional ranges for the distillate and residue of extractive distillation column 124 are shown in Table 1. Components other than those listed in Table 1 may also be present in the residue and distillate.

TABLE 1

EXTRACTIVE DISTILLATION COLUMN

|  | Conc. (wt. %) | Conc. (wt. %) | Conc. (wt. %) |
|---|---|---|---|
| Distillate |  |  |  |
| Methyl Acetate | 0.001 to 5 | 0.01 to 3 | 0 to 1 |
| Methyl Iodide | 5 to 65 | 15 to 55 | 25 to 40 |
| Water | 0.01 to 10 | 0.01 to 3 | 0 to 1 |
| PRC's | 0 to 25 | 0 to 20 | 5 to 15 |
| Dimethyl ether | 0 to 70 | 0 to 65 | 0 to 55 |
| Residue |  |  |  |
| Methyl Acetate | 0.001 to 5 | 0.01 to 3 | 0 to 1 |
| Methyl Iodide | 0 to 0.5 | 0 to 0.1 | 0 to 0.01 |
| Water | 20 to 90 | 30 to 85 | 40 to 85 |
| PRC's | 1 to 50 | 1.5 to 35 | 5 to 25 |
| Dimethyl ether | 0.001 to 5 | 0.01 to 3 | 0 to 1 |

In one embodiment, distillate stream 134 may be combined with raffinate stream 140 or bottoms stream 128 prior to returning to the carbonylation process.

Residue 136 is directed to recovery column 148 to produce a purified PRC's product stream in line 150 and second residue stream 152 comprising the extractive agent. Second residue stream 152 may be recycled directly to extractive distillation column 124', or preferably is combined with extractive agent feed stream 146 and fed to extractive distillation column 124'.

In one embodiment, the extractive agent is recovered from residue 136 to yield a PRC's product stream having a reduced water content. Residue 136 preferably is fed to recovery column 148 to produce an overhead PRC's product stream 150 and a bottoms stream 152. The overhead PRC's product stream 150 is enriched with PRC's, preferably acetaldehyde, with respect to bottoms stream 152. Overhead PRC's product stream 150 is deficient with methyl acetate, methanol, water and/or acetic acid, and more preferably deficient in all four, with respect to residue in stream 136, aqueous stream 142, or stream 132. In one embodiment, the overhead PRC's product stream 150 comprises less than 50 wt. % water, e.g., less than 25 wt. % or less than 10 wt. %. The bottoms stream 152 comprises the extractive agent and can be, and preferably is, recycled back to extractive distillation column 124' or to the carbonylation process to maintain water balance. Preferably, bottoms stream 152 comprises water.

Overhead PRC's product stream 150 may be condensed and refluxed, for example, at a ratio from 30:1 to 1:30, e.g., from 25:1 to 1:25 or from 1:5 to 5:1. When recovery column 148 is operated at 102 kPa, the temperature of the overhead PRC's stream existing in line 150 preferably is from 0° C. to 60° C., e.g., from 5° C. to 40° C. or from 10° C. to 30° C. The residue in line 152 may comprise the extractive agent. The temperature of the residue exiting in line 152 preferably is from 40° C. to 140° C., e.g., from 60° C. to 120° C. or from 80° C. to 100° C. In some embodiments, the pressure of recovery column 148 may range from 70 kPa to 400 kPa, e.g., from 90 kPa to 350 kPa or from 100 kPa to 300 kPa.

As indicated above, the residue in line 136 fed to recovery column 148 contains significantly reduced amount of alkyl halides than aqueous stream 142, and thus the overhead PRC stream 150 also contains little to no alkyl halides. In one embodiment, the overhead PRC stream comprises less than 10 wt. % of alkyl halides, e.g., less than 5 wt. % or less than 1 wt. %. In one embodiment, the overhead PRC stream 150 comprises less than 500 wppm of alkyl halides, e.g., less than 200 wppm or less than 100 wppm. In one embodiment, the overhead PRC stream 150 may be used in other processes that require PRC's.

In order that the invention disclosed herein may be more efficiently understood, examples are provided below. It should be understood that these examples are for illustrative purposes only and are not to be construed as limiting the invention in any manner.

EXAMPLES

Example 1

A simulation of a process in accordance with the embodiment of FIG. 2 was conducted using ASPEN™ software. The simulation utilized aqueous feed stream 142 as discussed above. An extractive agent, comprising water, was fed above the feedpoint of the aqueous feed stream. The compositions of the various streams of extractive distillation column 124' and recovery column 148 are shown in Table 2.

TABLE 2

| Composition | Feed Stream (wt. %) | Extractive Column (wt. %) | | Distillation Column (wt. %) | |
|---|---|---|---|---|---|
| | | Distillate | Residue | PRC's stream | Residue |
| Methyl Acetate | 0.1 | 0.0 | 0.0 | 0.2 | 0.0 |
| Methyl Iodide | 0.9 | 34.8 | 0.0 | 0.1 | 0.0 |
| Water | 66.6 | 0.6 | 77.4 | 0.1 | 99.9 |
| Acetaldehyde | 31.0 | 10.5 | 22.4 | 98.9 | 0.1 |
| Dimethyl Ether | 1.5 | 54.1 | 0.2 | 0.7 | 0.0 |

As shown by the simulation, the purified PRC's stream comprises 98.9 wt. % acetaldehyde and less than 1.1 wt. % of combined methyl acetate, methyl iodide, water, and dimethyl ether. Thus, a purified PRC's stream can be effectively separated in accordance with the present invention to achieve a purified PRC's stream comprising over 98 wt. % acetaldehyde.

While the invention has been described in detail, modifications within the spirit and scope of the invention will be readily apparent to those of skill in the art. In addition, it should be understood that aspects of the invention and portions of various embodiments and various features recited above and/or in the appended claims may be combined or interchanged either in whole or in part. In the foregoing descriptions of the various embodiments, those embodiments which refer to another embodiment may be appropriately combined with other embodiments as will be appreciated by one of skill in the art. Furthermore, those of ordinary skill in the art will appreciate that the foregoing description is by way of example only, and is not intended to limit the invention.

We claim:

1. A process for recovering permanganate reducing compounds (PRC's) from a crude acetic acid composition, the process comprising the steps of:
   separating the crude acetic acid composition in a light ends column into an overhead stream comprising methyl iodide, water, methyl acetate, and at least one PRC, and an acetic acid product stream;
   separating a portion of the overhead stream using a first distillation column to obtain a stream enriched in the at least one PRC, wherein the enriched stream further comprises at least some of the methyl iodide from the overhead stream; and
   separating a portion of the enriched stream in a second distillation column to obtain a distillate comprising methyl iodide and a residue comprising the at least one PRC, wherein the ratio of methyl iodide to PRC's in the residue is less than the ratio of methyl iodide to PRC's in the enriched stream.

2. The process of claim 1, further comprising the step of using an extractive agent in the second distillation column to extract at least one PRC into the residue.

3. The process of claim 2, wherein a mass flow ratio of the portion of the enriched stream and the extractive agent is at least 0.01:1.

4. The process of claim 2, further comprising recovering the extractive agent from the residue to yield a PRC's product that is reduced in water content.

5. The process of claim 2, wherein the extractive agent is selected from the group consisting of water, glycols, glycerol, high boiling alcohols, and mixtures thereof.

6. The process of claim 1, wherein the residue comprises less than 1 wt. % methyl iodide.

7. The process of claim 1, further comprising returning at least a portion of the distillate to a carbonylation process for producing the crude acetic acid composition.

8. The process of claim 1, wherein the distillate comprises less of the at least one PRC than the enriched stream, based on relative mass flow.

9. The process of claim 1, wherein the overhead stream further comprises at least one alkyl iodide selected from the group consisting of ethyl iodide, propyl iodide, butyl iodide, pentyl iodide, hexyl iodide, and isomers and mixtures thereof.

10. The process of claim 1, wherein at least 80% of the methyl iodide in the portion of the enriched stream is separated into the distillate.

11. The process of claim 1, wherein at least 80% of the at least one PRC in the portion of the enriched stream is separated into the residue.

12. The process of claim 1, wherein the at least one PRC is selected from the group consisting of acetaldehyde, acetone, methyl ethyl ketone, butyraldehyde, crotonaldehyde, 2-ethyl crotonaldehyde, 2-ethyl butyraldehyde, aldol condensation products thereof, and mixtures thereof.

13. The process of claim 1, further comprising the step of extracting the enriched stream in a liquid-liquid extractor with an extractive solvent to obtain a PRC's stream and a raffinate comprising methyl iodide, wherein the PRC's stream comprises the at least one PRC and from 0.01 to 5 wt. % methyl iodide, and wherein the portion of the enriched stream comprises the PRC's stream.

14. The process of claim 13, wherein the liquid-liquid extractive solvent comprises water.

15. The process of claim 1, further comprising condensing and biphasically separating the overhead stream into a heavy phase and a light phase.

16. The process of claim 15, further comprising separating the light phase in the one or more distillation columns to obtain the enriched stream.

17. The process of claim 15, further comprising separating the heavy phase in the one or more distillation columns to obtain the enriched stream.

18. A process for recovering permanganate reducing compounds (PRC's) from a crude acetic acid composition, the process comprising the steps of:
   separating the crude acetic acid composition in a light ends column into an overhead stream comprising methyl iodide, water, methyl acetate, and at least one PRC, and an acetic acid product stream;
   separating a portion of the overhead stream using one or more distillation columns to obtain a stream enriched in the at least one PRC, wherein the enriched stream further comprises at least some of the methyl iodide from the overhead stream;
   extracting the enriched stream in a liquid-liquid extractor with an extractive solvent to obtain a PRC's stream and a raffinate comprising methyl iodide, wherein the PRC's stream comprises the at least one PRC and from 0.01 to 5 wt. % methyl iodide; and
   separating a portion of the PRC's stream in an extractive distillation column using an extractive agent to obtain a distillate comprising methyl iodide and a residue comprising the at least one PRC and extractive agent, wherein the ratio of methyl iodide to PRC's in the residue is less than the ratio of methyl iodide to PRC's in the PRC's stream.

19. The process of claim 18, further comprising condensing and biphasically separating the overhead stream into a heavy phase and a light phase.

20. The process of claim 19, further comprising separating the light phase in the one or more distillation columns to obtain the enriched stream.

21. The process of claim 19, further comprising separating the heavy phase in the one or more distillation columns to obtain the enriched stream.

\* \* \* \* \*